(12) United States Patent
Surowitz

(10) Patent No.: US 6,485,459 B1
(45) Date of Patent: Nov. 26, 2002

(54) RETRACTABLE NON-REUSABLE NEEDLE

(76) Inventor: Joshua Surowitz, 2185 Radnor Ct., Juno Isles, FL (US) 33408

( * ) Notice: Subject to any disclaimer, the term of this patent is extended or adjusted under 35 U.S.C. 154(b) by 0 days.

(21) Appl. No.: 09/643,846

(22) Filed: Aug. 23, 2000

Related U.S. Application Data

(60) Provisional application No. 60/150,356, filed on Aug. 24, 1999.

(51) Int. Cl.$^7$ ................................................. A61M 5/00
(52) U.S. Cl. ..................... 604/110; 604/195; 604/218; 604/228; 604/243
(58) Field of Search ............................. 604/93.01, 110, 604/181, 187, 195, 218, 221, 222, 239, 243, 257, 264, 240, 272, 228

(56) References Cited

U.S. PATENT DOCUMENTS 5,085,638 A * 2/1992 Farbstein et al. ........... 128/919
5,382,235 A * 1/1995 Sak ............................. 604/110
5,964,735 A * 10/1999 Alexander .................. 604/110

* cited by examiner

Primary Examiner—Michael J. Hayes
(74) Attorney, Agent, or Firm—Warren Taltavull; Manelli Denison & Selter PLLC

(57) ABSTRACT

A syringe includes a needle mounted in a frangible plug at the tip thereof and is equipped with a plunger having a stopper at one end thereof with the end of the plunger having an opening for capturing the end of the needle that projects into the barrel of the syringe to allow the plunger to capture the needle so that when the plunger is retracted the needle will be withdrawn into the barrel of the syringe; the end of the plunger is also equipped with a stopper which is mounted on a section that is connected to the plunger through frangible links whereby when the plunger is withdrawn a selected distance, the links will be severed to retain the plunger and captured needle within the barrel.

11 Claims, 3 Drawing Sheets

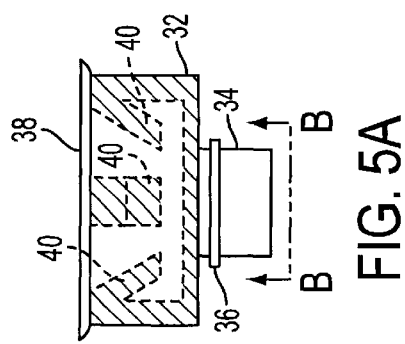
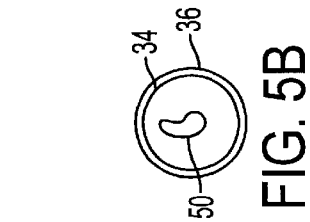
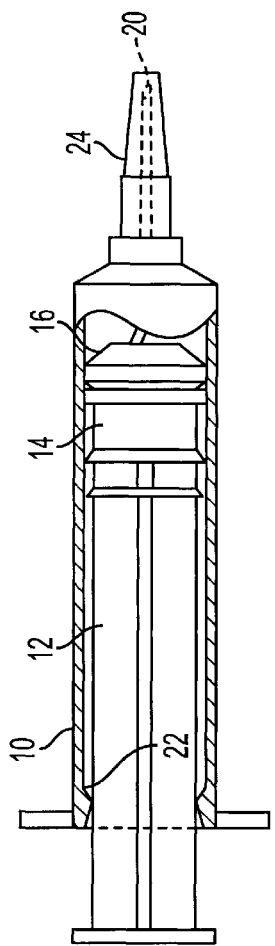
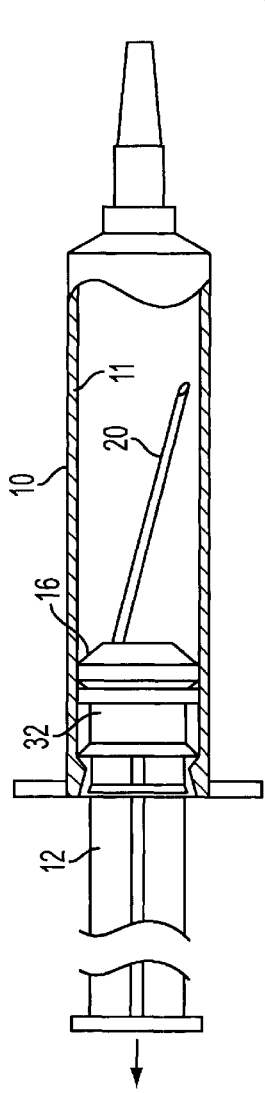
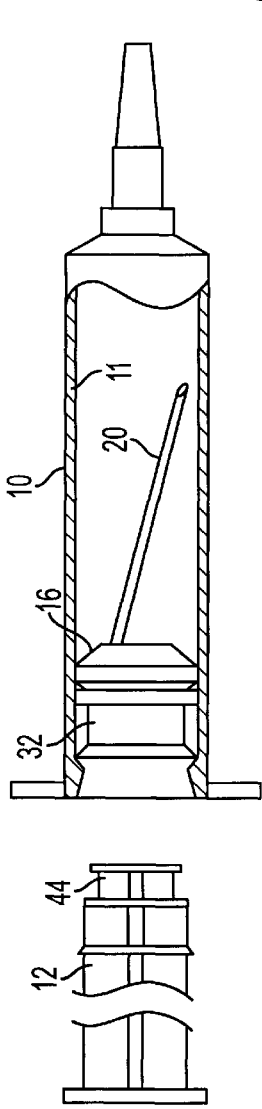

RETRACTABLE NON-REUSABLE NEEDLE

This application claims benefit of provisional application 60/150,356 filed Aug. 24, 1999.

FIELD OF THE INVENTION

The present invention relates to hypodermic syringes having a retractable needle to prevent accidental puncture of patients or medical personnel after use of the syringe. More particularly, the invention provides a fail safe structure for withdrawing the needle into the barrel of the syringe after use in such a way as to prevent subsequent access to the needle except by destruction of the barrel.

BACKGROUND OF THE INVENTION

The existence of a number of highly infectious viral diseases to which medical personnel in hospitals and clinics are exposed has prompted the development of a number of different types of safety features in medical devices and particularly in hypodermic syringes. The reason for this is that accidental puncture with the needle in the use of a syringes is a frequent cause for transmission of infection and one that can be avoided by proper and careful handling steps that are required. However, such steps often take additional time which medical personnel do not have especially when functioning under emergency circumstances.

To accommodate the frequent emergency situations in which hypodermic syringes are used, the prior art has developed a number of different structures for preventing post use accidents. Several of these techniques have employed shields which are placed over the used needle typically in a non-removable manner. These solutions suffer from the disadvantage that the user must carefully insert the shield while avoiding the puncture and this typically results in additional loss of time. Other techniques employ the retraction principal where the user pulls the needle back into the barrel. While this is useful in terms of safety and requires less time, the prior art structures have been generally impractical to manufacture at low expense and some have not safely maintained the needle in a non-accessible position.

Present manufacturing techniques for mass producing hypodermic syringes of the disposable type must meet a number of strict manufacturing standards to qualify for medical use. Further, the manufacturing steps required should be the minimum necessary to qualify for medical use and still be consistent with the disposable character of the article. Also, it is highly desirable that the retracted needle be inaccessible except through destruction of the barrel to lessen or eliminate subsequent improper use of the syringe.

A number of the hypodermic syringe structures proposed in the prior art unfortunately require unduly complicated manufacturing techniques which materially increase the cost of the syringes. Other procedures require a complete redesign of the existing manufacturing lines and thus discourage their widespread implementation.

SUMMARY OF THE INVENTION

The present invention provides an effective retraction structure for hypodermic syringes that positively blocks access to the used needle once retraction has been effected. Moreover, the structure of the present invention will not materially increase the cost of the disposable type syringes while affording added protection to medical workers and patients working in connection with infectious diseases. Additionally, the structure of the hypodermic syringe of the present invention can be easily manufactured with a modest restructure of existing manufacturing facilities.

In a preferred form, the present invention utilizes a needle carrying hub where the needle extends beyond the rear face of the hub a limited distance and which is retained in the hub outlet channel by an easily frangible adhesive. When the plunger of the syringe is pushed into the barrel to discharge the contents of the barrel, a locking member mounted on the forward end of the plunger engages the projecting end of the needle and holds the end of the needle to allow the user to retract the needle by retracting the plunger which action breaks the frangible adhesive. At a point along the barrel, a detent is located which engages a portion of the locking member as the plunger with the needle is retracted. The detent prevents further movement of the locking member and effects breakage of the connection between the plunger end and the locking member thus preventing issuance of the retracted needle by the plunger.

BRIEF DESCRIPTION OF THE DRAWINGS

FIGS. 1A, 1B and 1C are side views in elevation, partly in section, showing the syringe of the present invention in three positions of the plunger in the barrel of the syringe;

FIG. 5A is an enlarged view of the locking device; and FIG. 5B is an end view taken along lines 5B—5B of FIG. 5A.

DETAILED DESCRIPTION OF THE INVENTION

Figure 2A:
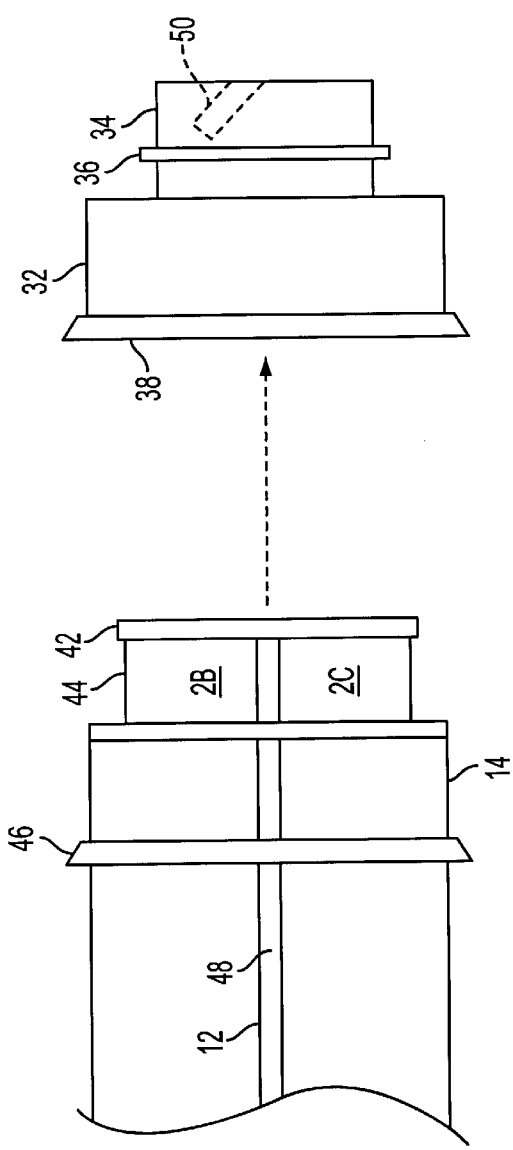
FIG. 2A is an exploded view of the forward end of the plunger and the locking member of this invention.
Figure 4:
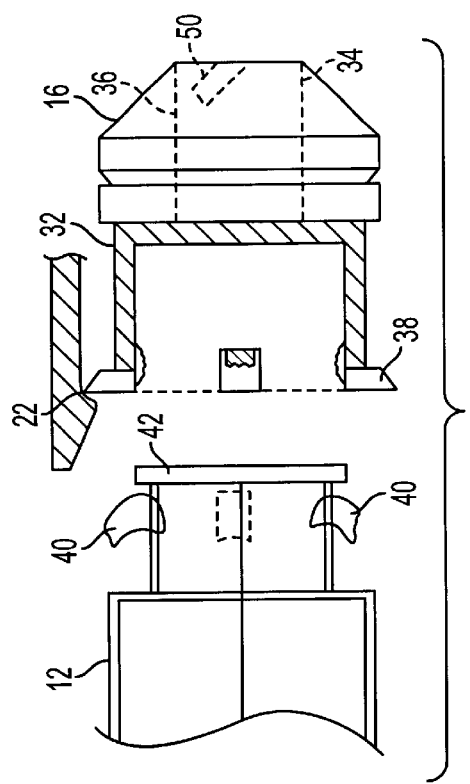
FIG. 4 is sectional view of the locking member of the present invention in locking engagement with the locking annulus.

Referring to the accompanying drawings, there is shown in FIGS. 1A–1C, the retraction operation using the syringe 10 of this invention. In FIG. 1A, it will be seen that the syringe 10 is provided with a plunger 12 having a forward end 14 to which is removably attached the locking member 32 on which is mounted a flexible seal plug or stopper 16. The locking member engages the inner end 26 of a needle cannula 20, as explained below. Upon withdrawal of the plunger 12, the needle 20 is pulled into the hub 24 of the syringe and into the barrel 11 of the syringe 10 to the position shown in FIG. 1B. Continued pulling on the plunger 12 will effect separation of the locking member 32 from the end 44 of the plunger leaving the needle, as shown in FIG. 1C, lying at an angle to the longitudinal axis of the barrel 11 to prevent re-insertion into the bore in the adhesive plug at the forward end of the barrel 11. Generally, a user need not exercise the option of separating the plunger from the tip since user safety is achieved by simply pulling the needle into the barrel 11 of the syringe. In some cases, however, additional safety is afforded by pulling on the plunger to effect the separation of the needle from the plunger tip.

Figure 3:
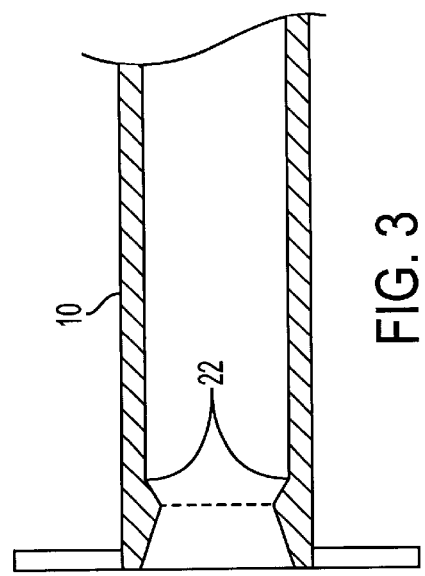
FIG. 3 is a view of the rear end of the syringe barrel showing the detent annulus.

In FIG. 2A, there is shown an exploded view of the end 14 of the plunger 12 and the locking member 32. The member 32 includes a tubular extension 34 provided with an annulus 36 to allow frictional engagement with the interior bore of the plug 16. The rear edge of the member 32 is provided with a radially projecting annular ring 38 which is dimensioned to ensure contact with the stop member 22 which is formed integrally on the interior of the barrel 11 of the syringe 10 as shown in FIG. 3. Preferably, the stop member or members are spaced about the axis of the barrel and may take the form of an annular projection with an abutment surface that extends at an angle to the longitudinal axis of the barrel 11.

Figure 2B:
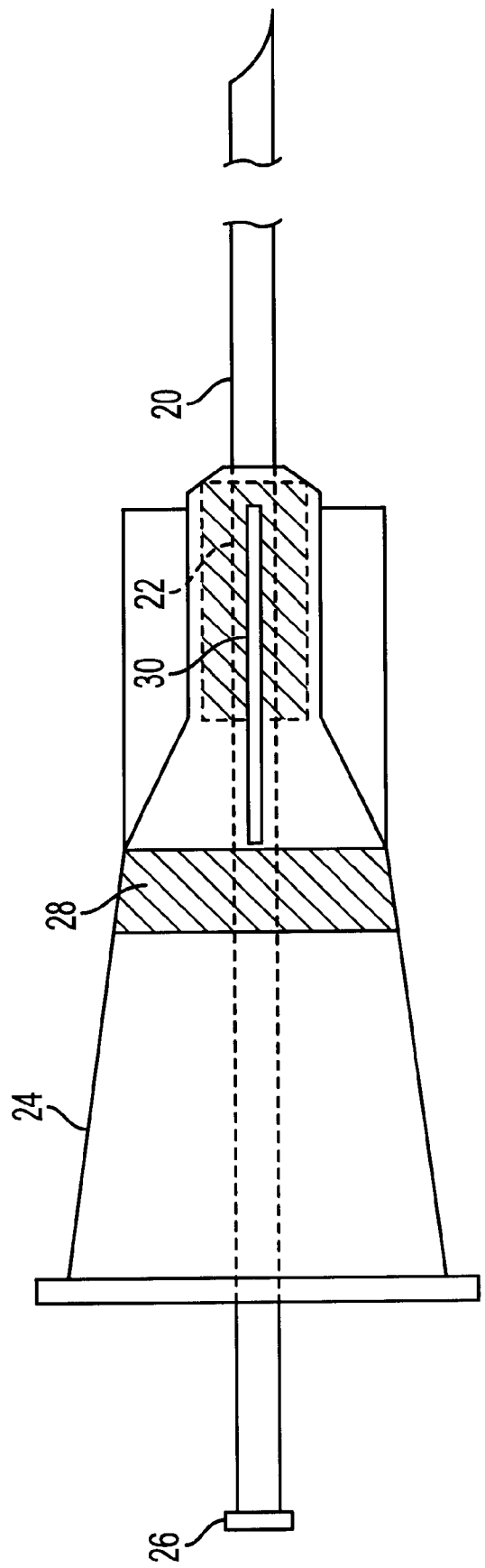
FIG. 2B is a side view partly in section of needle used in the present invention.

In FIG. 2B, there is shown an enlarged view of the needle 20 carried in a hub 24 by means of spaced apart sealing plug 28. Plug 30 is preferably frangible such as polystyrene plugs and which surround and provide resistance to movement of the needle when the needle is injected into the skin of a patient or into a vessel containing medication. Plug 28 serves as a liquid seal to prevent any discharge from the needle when the needle is withdrawn into the barrel so that no withdrawn specimen can escape. The hub 24 is generally conical in section to allow ease of placement on the tip of the syringe 10.

After administration of a medicine or drawing of a specimen, the plunger will be projected forward so that the forward end of the locking member 32 which is surrounded by the rubber plug 16 will engage in its curved recess 50 the enlarged end 26 of the needle 20. A locking mechanism for the end 26 is shown in FIG. 5B which is an end view of the tip 34 of the locking mechanism. Proper dimensioning of the recess 50 will securely lock the needle to the tip 34. For example, as shown in FIG. 5B, the recess 50 tapers away from its central axis so as to wedge the end 26 of the needle into firm engagement in the recess 50. Thereafter, the plunger may be pulled back, as shown in FIG. 1C, to withdraw the needle into the barrel 11. The end 14 of the plunger is secured to the locking member 32 by virtue of engagement of the flange 42 on extension 44 with flexible, frangible fingers 40, which serve as severable connecting members, as shown in FIG. 5. When the plunger is withdrawn so that the ring 38 engages the abutment surface or stop 22 which serves as a separating member, continued pulling on the plunger will effect breaking of the fingers 40 and separation of the plunger from the receiving portion of the locking member 32 leaving the needle in the barrel 11.

The syringe and its parts can be made of plastic as is conventional with the needle being metal and the plug 16 of resilient neoprene or rubber.

What is claimed is:

1. A syringe having a barrel including an interior wall, one end being open and receiving a plunger, the other end having a shape for supporting a member that removably supports a needle with said needle having an enlarged end of a selected size and including a centrally located passage, said plunger including at one end thereof a stopper for sealingly engaging the interior wall of said barrel, said stopper having an end including a needle capture opening for receiving and locking said enlarged end of said needle in said opening upon engagement of said opening with the end of a needle removably supported on said member, said needle capture opening being in the shape of a curved recess having a central axis and that tapers away from said central axis so as to wedge the end of said needle in said recess and having a portion of a size to receive said enlarged end of said needle, said stopper being carried on said one end of said plunger by a severable connecting member, said barrel including at least one separating member for separating said stopper from said first end of said plunger when said one end is withdrawn from said barrel past said separating member.

2. The syringe as claimed in claim 1 wherein said member that removably supports the needle comprises a bore through which a needle extends, a frangible plug retaining the needle in place in said bore.

3. The syringe as claimed in claim 2 wherein said plug is polystyrene.

4. The syringe as claimed in claim 1 wherein said needle capture opening leads to a bore having a bottom portion in said stopper member.

5. The syringe as claimed in claim 1 wherein said stopper has a receiving portion shaped to receive said one end of said plunger.

6. The syringe as claimed in claim 5 wherein said connecting member is a frangible finger extending from an end portion of said plunger.

7. The syringe as claimed in claim 6 wherein a plurality of fingers are provided about said one end of said plunger.

8. The syringe as claimed in claim 1 wherein said stopper comprises a locking member on which a flexible plug is mounted.

9. The syringe as claimed in claim 8 wherein said locking member has a rear end and a ring extending radially from said rear end to engage the interior wall of said barrel, said barrel having on said interior wall adjacent said open end thereof a plurality of said separating members spaced about said interior wall.

10. The syringe as claimed in claim 1 wherein said separating members are each annular projections with an abutment surface extending at an angle to the longitudinal axis of said barrel.

11. A syringe having a barrel including an interior wall, one end being open and receiving a plunger, the other end having a shape for supporting a member that removably supports a needle with said needle having an enlarged end of a selected size and including a centrally located passage, said plunger including at one end thereof a stopper for sealingly engaging the interior wall of said barrel, said stopper having an end including a needle capture opening for receiving and locking said enlarged end of said needle in said opening upon engagement of said opening with the end of a needle removably supported on said member, said needle capture opening being in the shape of a curved recess and having a portion of a size to receive said enlarged end of said needle, said stopper including a receiving portion for receiving said one end of said plunger and being carried on said one end of said plunger by a plurality of frangible fingers extending from said one end of said plunger into said receiving portion of said stopper, said barrel including at least one separating member for separating said stopper from said first end of said plunger when said first end is withdrawn from said barrel past said separating member.

* * * * *